United States Patent [19]

Huang et al.

[11] Patent Number: 4,496,541
[45] Date of Patent: Jan. 29, 1985

[54] COMPOUNDS FOR TREATING HYPERTENSION

[75] Inventors: Fu-chih Huang, Boonton, N.J.; Howard Jones, Ossining; Clara Lin; Bernard Loev, both of Scarsdale, all of N.Y.

[73] Assignee: USV Pharmaceutical Corporation, Tarrytown, N.Y.

[21] Appl. No.: 457,611

[22] Filed: Jan. 12, 1983

[51] Int. Cl.³ ..................... A61K 37/00; C07C 103/50
[52] U.S. Cl. ................................... 514/2; 260/112.5 R
[58] Field of Search .................. 260/112.5 R; 424/177

[56] References Cited

U.S. PATENT DOCUMENTS 4,374,829 2/1983 Harris et al. ................. 260/112.5 R

FOREIGN PATENT DOCUMENTS 2095682 10/1982 United Kingdom ......... 260/112.5 R

Primary Examiner—Delbert R. Phillips

[57] ABSTRACT

Compounds of the general formula

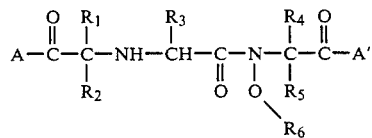

and their pharmaceutically-acceptable salts, wherein the substituents are as defined herein, having antihypertensive activity.

16 Claims, No Drawings

COMPOUNDS FOR TREATING HYPERTENSION

BACKGROUND OF THE INVENTION

This application relates to compounds, their pharmaceutically-acceptable salts, and pharmaceutical preparations made therefrom, having biological utility in the treatment of hypertension in subjects suffering therefrom.

SUMMARY OF THE INVENTION

Broadly stated, the present invention comprises compounds of the formula

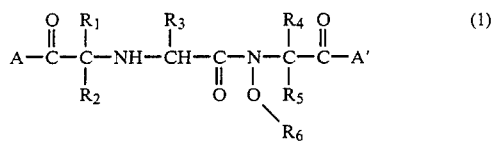

and their pharmaceutically-acceptable salts,
wherein

A and A' are independently hydroxy, alkoxy, aryloxy, or hydroxyamino;

$R_1$, $R_2$, $R_4$, and $R_5$ are independently hydrogen, alkyl, aryl, aralkyl, fused cycloalkyl-aryl, fused arylcycloalkyl, aryloxyalkyl, or arylalkyloxyalkyl;

$R_3$ is hydrogen, lower alkyl, lower alkenyl, lower alkynyl, aryl, fused cycloalkyl-aryl, fused aryl-cycloalkyl, fused cycloalkylaryl-alkyl, fused aryl-cycloalkyl-alkyl, aralkyl, cycloalkyl, or heterocyclic; and $R_6$ is $(CH_2)_nX$ wherein n is 0-2 and X is hydrogen, alkyl, alkenyl, alkynyl, acyl, cycloalkyl, cycloalkylalkyl, polycycloalkyl, polycycloalkyl-alkyl, aryl, aralkyl, polycyclic aryl, fused cycloalkyl-aryl, fused arylcycloalkyl, fused aryl-cycloalkyl-alkyl, or fused cycloalkyl-aryl-alkyl;

wherein the alkyl, alkoxy, alkenoxy, alkenyl, and alkynyl groups may carry substituents selected from the group consisting of hydroxy, acyloxy, aryl, alkoxy, aryloxy, amino, mono- or dialkylamino, acylamino, mercapto, mercaptoalkyl, and alkylthio; the cycloalkyl rings may include one or two hetero atoms, may be saturated or unsaturated, and may carry substituents selected from the group consisting of alkyl, hydroxy, alkylamino, and nitro; and the aryl rings may contain a hetero atom and may carry substituents selected from the group consisting of carboxylic acid, cyano, carbolower alkoxy, alkyl, hydroxy, alkoxy, hydroxyalkyl, halo, haloalkyl, mercapto, mercaptoalkyl, alkylthio, amino, alkylamino, aminoalkyl, nitro, methylenedioxy, and sulfamyl;

wherein the alkyl groups contain 1 to 9 carbon atoms; and the cycloalkyl groups and the cycloalkyl portions of substituents containing cycloalkyl groups contain 3 to 9 carbon atoms.

DESCRIPTION OF THE PREFERRED EMBODIMENTS

Preferred compounds of the present invention are those of the general formula given above in which A and A' are independently hydroxy or lower alkoxy; $R_1$, $R_2$, $R_3$, $R_4$, and $R_5$ are each hydrogen, alkyl, aryl, aralkyl, or w-amino alkyl wherein the amino is mono- or disubstituted with hydrogen, alkyl, aryl, or aralkyl, or is incorporated in a saturated or unsaturated one- or two-ring heterocyclic moiety containing preferably up to 12 atoms in the ring; and $R_6$ is $(CH_2)_nX$ wherein n is 0-2 and X is hydrogen, alkyl, aryl, aralkyl, cycloalkyl, alkoxyalkyl, aminoalkyl, heteroaryl, heteroaralkyl, or fused aryl-aryl, any of which can be substituted or unsubstituted. Included as preferred groups are groups in which $R_6$ provides diuretic activity to the compound (1), e.g., sulfamylchloro-phenyl.

The alkyl groups per se and the alkyl moieties in alkoxy, aralkyl, cycloalkyl, aminoalkyl, and the like, may be straight-chained or branched and preferably contain from 1 to 9 carbon atoms. Such groups include methyl, ethyl, propyl, isopropyl, butyl, isobutyl, tertiary-butyl, amyl, iso-amyl, hexyl, octyl, and the like. Preferably the alkyl groups are lower alkyl, which term shall refer to alkyl groups containing from 1 to 6 carbon atoms, straight-chained or branched.

The alkenyl and alkynyl groups and moieties can also be straight or branched-chained groups containing from 2 to 9, and preferably 2 to 6, carbon atoms. Such groups include vinyl, ethynyl, propenyl, isopropenyl, and the like.

The acyl groups include such groups as alkanoyl, aroyl, and aralkanoyl, wherein the alkyl and aryl moieties are as defined herein, as well as sulfonyl, sulfamoyl, carbamoyl, and the like, optionally containing an alkyl moiety with 1 to 9 and preferably 1 to 6 carbon atoms.

The preferred substituents on the above alkyl, alkenyl, alkynyl, and acyl groups include hydroxy, alkoxy, amino, alkylamino, dialkylamino, mercapto, alkylmercapto, and the like.

The cycloalkyl groups and moieties are saturated or unsaturated and preferably contain 3 to 9 carbon atoms. By "polycycloalkyl" is meant 2 or more fused cycloalkyl rings, having a total of up to 20 carbon atoms. The cycloalkyl, polycycloalkyl, polycyclic aryl, and fused aryl-cycloalkyl structures can also contain one or two hetero atoms, i.e., a sulfur, oxygen, or nitrogen atom, thereby forming a hetero-ring.

Preferred cyclic and polycyclic ring structures include such radicals as cyclopropyl, cyclobutyl, cyclopentyl, cyclohexyl, cycloheptyl, adamantyl, norbornyl, phenyl, tolyl, benzyl, phenethyl, indolyl, dimethoxyphenyl, hydroxybenzyl, indanyl, naphthyl, tetrahydronaphthyl, decanhydronaphthyl, pyridyl, quinolyl, guanidino, pyrrolidyl, pyrrolyl, morpholinyl, furyl, furfuryl, tetrahydrofurfuryl, benzimidazolyl, thienyl, imidazolyl, and the like. Preferred substituents on the aryl, cycloalkyl, fused aryl-aryl, fused arylcycloalkyl, and polycyclic ring structures include hydroxy, alkyl, alkoxy, aryl, aryloxy, aralkyl, alkylamino, dialkylamino, alkenyl, alkynyl, carboxy, carboalkoxy, cyano, mercapto, amino, alkylmercapto, halo, trifluoromethyl, sulfonamide, and the like.

The halo groups include fluoro, chloro, bromo and iodo. Preferred hetero atoms are S, O, and N.

Substituents which are "unsaturated" contain one or more double or triple bond.

Compounds in accordance with the present invention are readily prepared employing known starting materials and procedures. It will be understood by those skilled in the art that the carbons to which $R_1$ and $R_3$ are attached can be asymmetric centers, such that the inventive compounds may exist in SS, SR, RS, and RR forms. Individual isomers and diastereoisomeric mixtures of said forms are within the scope of the invention. The preferred forms have (S,S) configuration.

The compounds of the formula (1) can be prepared by reacting a compound of the formula (2):

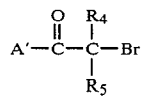 (2)

with a compound of the formula $R_6$—$ONH_2$ to form compound (3):

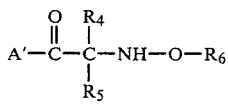 (3)

wherein $R_4$, $R_5$, $R_6$, and A' are as defined hereinabove and A' is an esterifying group such as —$OC(CH_3)_3$. Compound (3) is then reacted with an anhydride of the formula (4):

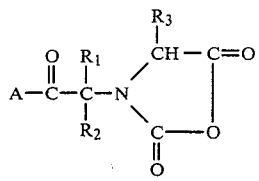 (4)

in which A, $R_1$, $R_2$, and $R_3$ are as defined above, to form a compound (5):

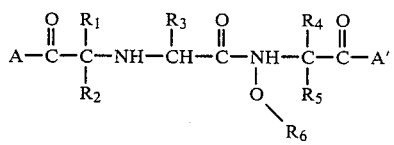 (5)

which is converted to the acid at A' by reaction with e.g. HCl. Compound (4) is obtained by reacting compound (6)

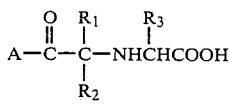 (6)

with an excess of phosgene in methylene chloride with heat and reflux.

As an alternate route to proceeding via compound (4), one can react compound (6) with e.g. isobutylene in dioxane to form compound (7)

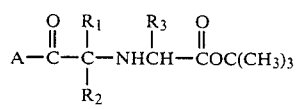 (7)

and then protecting the nitrogen by reaction with a suitable group such as 2,2,2-trichloroethyl chloroformate (8) in pyridine

 (8)

to form the protected ester (9):

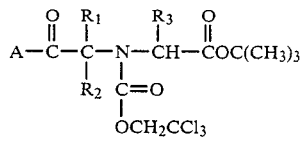 (9)

The ester group on compound (9) is converted to a carboxylic acid group by reaction with strong HCl in dioxane, then converted to the acid chloride by reaction with oxalyl chloride in methylene chloride. The resulting compound (10)

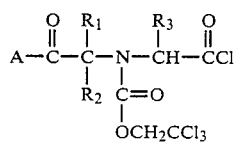 (10)

is reacted with compound (3) and the N-protecting group is removed with e.g. zinc dust in glacial acetic acid to form compound (5). Each of the above reactions proceeds in a straight-forward manner in a suitable solvent at temperatures ranging from 0° C. to 150° C.

The products are obtained typically as a mixture of diastereoisomers which can be separated by standard methods of fractional crystallization or chromatography.

The compounds of this invention form acid salts with various inorganic and organic acids which are also within the scope of the invention. The pharmaceutically-acceptable acid addition salts of the compounds of the present invention may be prepared by conventional reactions by reacting the free amino acid or amino ester with an appropriate acid providing the desired anion, either in a solvent or medium in which the salt is insoluble, or in water and removing the water by freeze-drying. The salts of strong acids are preferred. As exemplary, but not limiting, of pharmaceutically-acceptable acid salts are the salts of hydrochloric, hydrobromic, sulfuric, nitric, acetic, fumaric, malic, maleic and citric acids.

The action of the enzyme renin or angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds of this invention intervene in the renin-to-angiotensin I-to-angiotensin II sequence by inhibiting angiotensin I converting enzyme and reducing or eliminating the formation of the pressor substance angiotensin II and therefore are useful in reducing or relieving hypertension. Thus by the administration of a composition containing one or a combination of compounds of formula (1) or pharmaceutically-acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitonealy can also be employed.

The compounds of the present invention exhibit surprising and pronounced antihypertensive activity. When evaluated according to standard, recognized in vivo methods, a compound of the present invention in the (S,S) form and having the structure (10):

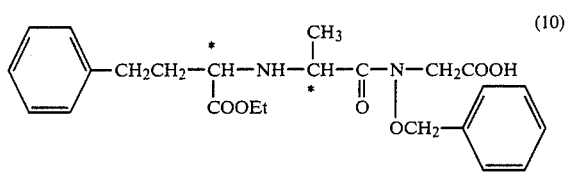

exhibited an angiotensin converting enzyme inhibition $ED_{50}$ value of less than 1 mg/kg.

The compounds of the invention can be utilized to achieve the reduction of blood pressure by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

Specific embodiments of the invention are illustrated in the following Examples.

EXAMPLE I

A mixture of 1.6 g of O-benzylhydroxylamine, 2.1 g of t-butylbromoacetate and 1.4 g of $K_2CO_3$ in 10 ml of dimethylformamide (DMF) was stirred overnight at room temperature. DMF was then removed in vacuo and the residue was extracted with ethyl acetate. The organic solution was evaporated to give 2 g of oily product, t-butyl-O-benzyl-α-hydroxylaminoacetic acetate,

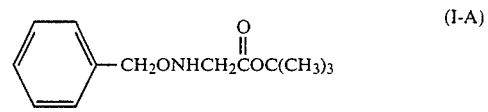

A mixture of N-[(1S)-1-ethoxycarbonyl-3-phenylpropyl]-L-alanine (2 g) and an excess of phosgene in 30 ml of methylene chloride was heated to reflux for 2 hours. Evaporation of solvent gave 2.1 g of N-[1-(S)-ethoxy carbonyl-3-phenylpropyl]-S-alanyl-N-carboxyanhydride A mixture of 1.6 g of this anhydride and 2.1 g of product (I-A) in 10 ml of methylene chloride was stirred overnight at room temperature. The organic solution was then washed with $NaHCO_3$ solution with water, and then dried and evaporated to dryness. Purification by dry column chromatography gave 1.1 g of oily product (I-B), O-benzyl-N-[N-[(1S)-1-ethoxycarbonyl-3-phenylpropyl]-L-alanyl]-α-[hydroxylamino]-acetic acid t-butyl ester,

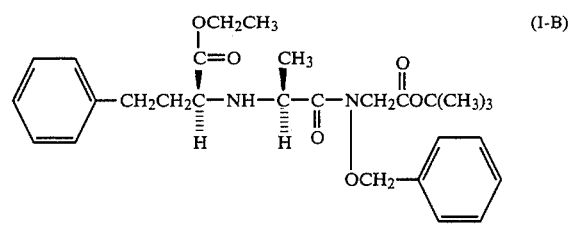

A solution of 1.1 g of product I-B in 100 ml of ether was bubbled with dry HCl gas at 0° C. for 2 hours. Evaporation of the ether gave 1.0 g of the hydrochloric acid salt (I-C), O-benzyl-N-[N-[(1S)-1-ethoxycarbonyl-3-phenylpropyl]-L-alanyl]-α-[hydroxylamino]-acetic acid-HCl salt, a white powder with a melting point of 72°–82° C. (dec.).

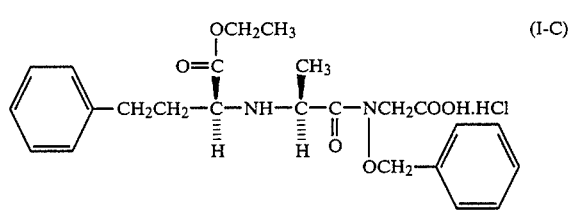

EXAMPLE II

The following compounds were prepared in a manner wholly analogous to that described in Example I:

O—Methyl-N—[N—[(1S)-1-ethoxycarbonyl-3-phenylpropyl]-L—alanyl]-α-[hydroxylamino]-acetic acid t-butyl ester (II-A)

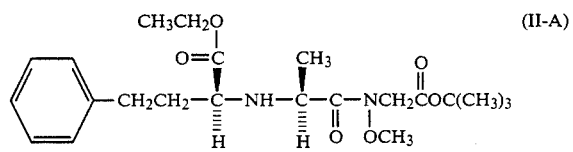

-continued

O—Methyl-N—[N—[(1S)-1-ethoxycarbonyl-3-phenylpropyl]-L—alanyl]-α-[hydroxylamino]-acetic acid, hydrochloric acid salt (II-B)

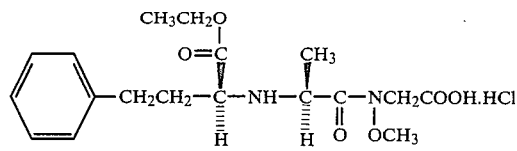
(II-B)

EXAMPLE III

The following compounds are prepared in a manner wholly analogous to that described in Example I:

O—Benzyl-N—[N—[(1S)-1-ethoxycarbonyl-3-phenylpropyl]-L—lysinyl]-α-[hydroxyamino]-acetic acid (III-A)

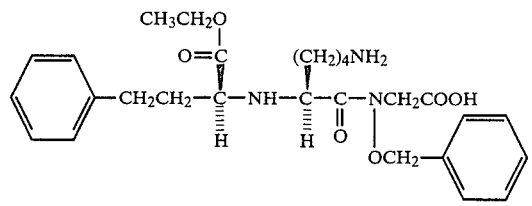

O—Benzyl-N—[N—[(1S)-1-ethoxycarbonyl-ethyl]-L—alanyl]-α-[hydroxylamino]-acetic acid (III-B)

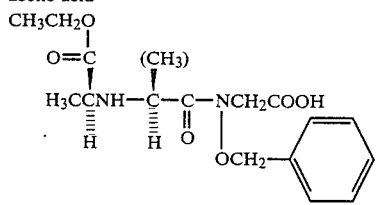

O—(4-Pyridylmethyl)-N—[N—[(1S)-1-ethoxycarbonyl-3-phenylpropyl]-L—alanyl]-α-[hydroxylamino]-acetic acid (III-C)

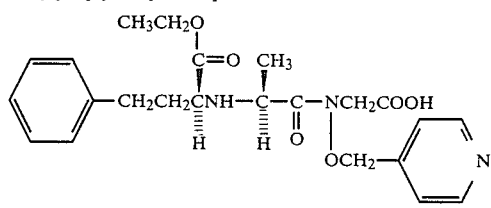

O—(Ethoxyethyl)-N—[N—[(1S)-1-ethoxycarbonyl-3-phenylpropyl]-L—alanyl]-α-[hydroxylamino]-acetic acid (III-D)

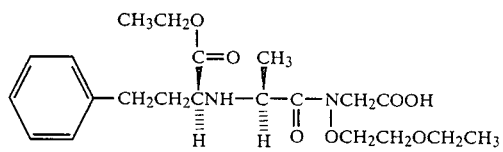

O—(Benzyl)-N—[N—[(1S)-1-ethoxycarbonyl-3-phenoxypropyl]-L—alanyl]-α-[hydroxylamino]-acetic acid (III-E)

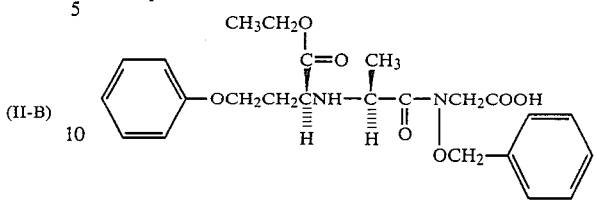

O—Benzyl-N—[N—[(1S)-1-ethoxycarbonyl-3-phenylpropyl]-L—alanyl]-α-[hydroxylamino]-propionic acid (III-F)

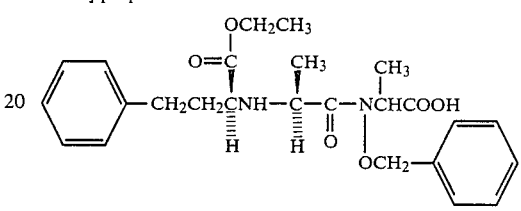

O—(1-Naphthylmethyl)-N—[N—[(1S)-1-ethoxycarbonyl-3-phenylpropyl]-L—alanyl]-α-[hydroxylamino]-acetic acid (III-G)

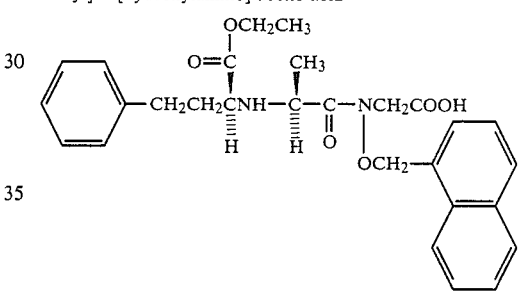

O—[N—Morpholinoethyl]-N—[N—[(1S)-ethoxycarbonyl-3-phenylpropyl]-L—alanyl]-α-[hydroxylamino]-acetic acid (III-H)

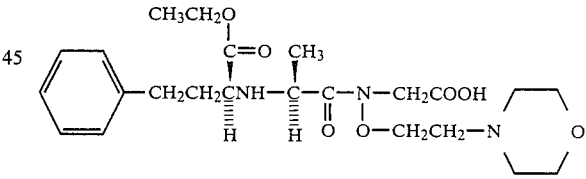

What is claimed is:
1. Compounds of the formula

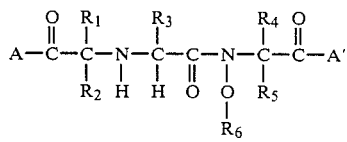

and their pharmaceutically-acceptable salts, wherein

A and A' are independently hydroxy, $C_1$-$C_9$ alkoxy, aryloxy, or hydroxyamino;

$R_2$, $R_4$ and $R_5$ are independently hydrogen, or $C_1$-$C_9$ alkyl;

$R_3$ is hydrogen, $C_1$-$C_9$ alkyl or ω-amino $C_1$-$C_9$ alkyl;

$R_1$ is phenyl $C_1$–$C_9$ alkyl, $C_1$–$C_9$ alkyl, $C_3$–$C_9$ cycloalkyl, fused cyclo $C_3$–$C_9$ alkylphenyl, or phenoxy $C_1$–$C_9$ alkyl; and $R_6$ is $(CH_2)_nX$ wherein n is 0–2 and X is hydrogen, $C_1$–$C_9$ alkyl, $C_1$–$C_9$ alkoxy, $C_3$–$C_9$ cycloalkyl, adamantyl, norbornyl, phenyl, tolyl, benzyl, phen $C_1$–$C_9$ alkyl, indolyl, dimethoxyphenyl, hydroxybenzyl, indanyl, naphthyl, tetrahydronaphthyl, decanhydronaphthyl, pyridyl, quinolyl, guanidino, pyrrolidyl, pyrrolyl, morpholinyl, furyl, furfuryl, tetrahydrofurfuryl, benzimidazolyl, thienyl, or imidazolyl.

2. Compounds according to claim 1 wherein

A and A' are independently hydroxy or $C_1$–$C_9$ alkoxy;

$R_2$, $R_4$ and $R_5$ are independently hydrogen or methyl;

$R_6$ is $(CH_2)_nX$ wherein n is 0–2; and

X is hydrogen, $C_1$–$C_9$ alkyl, phenyl, pyridyl, $C_1$–$C_9$ alkoxy, naphthyl, morpholino or phenyl $C_1$–$C_9$ alkyl.

3. The compound according to claim 2 which is O-benzyl-N-[N-[(1S)-1-ethoxycarbonyl-3-phenylpropyl]-L-alanyl]-α-[hydroxylamino]-acetic acid, and its pharmaceutically-acceptable salts.

4. The compound according to claim 2 which is O-benzyl-N-[N-[(1S)-1-ethoxycarbonyl-3-phenylpropyl]-L-alanyl]-α-[hydroxylamino]-acetic acid t-butyl ester, and its pharmaceutically-acceptable salts.

5. The compound according to claim 2 which is O-methyl-N-[N-[(1S)-1-ethoxycarbonyl-3-phenylpropyl]-L-alanyl]-α-[hydroxylamino]-acetic acid, and its pharmaceutically-acceptable salts.

6. The compound according to claim 2 which is O-methyl-N-[N-[(1S)-1-ethoxycarbonyl-3-phenylpropyl]-L-alanyl]-α-[hydroxylamino]-acetic acid t-butyl ester, and its pharmaceutically-acceptable salts.

7. The compound according to claim 2 which is O-benzyl-N-[N-[(1S)-1-ethoxycarbonyl-3-phenylpropyl]-L-lysinyl]-α-[hydroxylamino]-acetic acid, and its pharmaceutically-acceptable salts.

8. The compound according to claim 2 which is O-benzyl-N-[N-[(1S)-1-ethoxycarbonylethyl]-L-alanyl]-α-[hydroxylamino]-acetic acid, and its pharmaceutically-acceptable salts.

9. The compound according to claim 2 which is O-(4-pyridylmethyl)-N-[N-[(1S)-1-ethoxycarbonyl-3-phenylpropyl]-L-alanyl]-α-[hydroxylamino]-acetic acid and its pharmaceutically-acceptable salts.

10. The compound according to claim 2 which is O-(ethoxyethyl)-N-[N-[(1S)-1-ethoxycarbonyl-3-phenylpropyl]-L-alanyl]-α-[hydroxylamino]-acetic acid, and its pharmaceutically-acceptable salts.

11. The compound according to claim 2 which is O-benzyl-N-[N-[(1S)-1-ethoxycarbonyl-3-phenoxypropyl]-L-alanyl]-α-[hydroxylamino]-acetic acid, and its pharmaceutically-acceptable salts.

12. The compound according to claim 2 which is O-benzyl-N-[N-[(1S)-1-ethoxycarbonyl-3-phenylpropyl]-L-alanyl]-α-[hydroxylamino]-propionic acid, and its pharmaceutically-acceptable salts.

13. The compound according to claim 2 which is O-(1-Naphthylmethyl)-N-[N-[(1S)-1-ethoxycarbonyl-3-phenylpropyl]-L-alanyl]-α[hydroxylamino]-acetic acid, and its pharmaceutically-acceptable salts.

14. The compound according to claim 2 which is O-[N-Morpholinoethyl]-N-[N-[(1S)-ethoxycarbonyl-3-phenylpropyl]-L-alanyl]-α-[hydroxylamino]-acetic acid, and its pharmaceutically-acceptable salts.

15. A pharmaceutical preparation comprising one or more compounds or salts according to claim 1, in association with a pharmaceutically-acceptable carrier.

16. A method of alleviating hypertension in a host suffering therefrom, comprising administering to said host a therapeutically-effective amount of one or more compounds or salts according to claim 1.

* * * * *